United States Patent
Nobile et al.

(10) Patent No.: US 11,559,801 B2
(45) Date of Patent: *Jan. 24, 2023

(54) APPARATUS AND METHOD FOR CELL, SPORE, OR VIRUS CAPTURE AND DISRUPTION

(71) Applicant: Tangen Biosciences, Inc., Branford, CT (US)

(72) Inventors: John Richard Nobile, Guilford, CT (US); John F. Davidson, Guilford, CT (US)

(73) Assignee: TANGEN BIOSCIENCES, INC., Branford, CT (US)

( * ) Notice: Subject to any disclaimer, the term of this patent is extended or adjusted under 35 U.S.C. 154(b) by 918 days.

This patent is subject to a terminal disclaimer.

(21) Appl. No.: 15/522,039

(22) PCT Filed: Nov. 2, 2015

(86) PCT No.: PCT/US2015/058612
§ 371 (c)(1),
(2) Date: Apr. 26, 2017

(87) PCT Pub. No.: WO2016/073353
PCT Pub. Date: May 12, 2016

(65) Prior Publication Data
US 2017/0333891 A1 Nov. 23, 2017

Related U.S. Application Data

(60) Provisional application No. 62/074,325, filed on Nov. 3, 2014.

(51) Int. Cl.
*B01L 3/00* (2006.01)
*C12M 1/00* (2006.01)
(Continued)

(52) U.S. Cl.
CPC .............. *B01L 3/502* (2013.01); *B01F 31/86* (2022.01); *C12M 47/06* (2013.01); *C12N 1/06* (2013.01);
(Continued)

(58) Field of Classification Search
CPC ... C12N 1/06; C12M 47/06; B01F 2215/0037
See application file for complete search history.

(56) References Cited

U.S. PATENT DOCUMENTS

| | | |
|---|---|---|
| 4,261,474 A | 4/1981 | Cohen |
| 4,656,134 A | 4/1987 | Ringold |

(Continued)

FOREIGN PATENT DOCUMENTS

| | | |
|---|---|---|
| CN | 1564713 A | 1/2005 |
| CN | 101636230 A | 1/2010 |

(Continued)

OTHER PUBLICATIONS

International Search Report and Written Opinion dated Jul. 27, 2017 for PCT Application No. PCT/US2017/024455.

(Continued)

*Primary Examiner* — Robert J Yamasaki
(74) *Attorney, Agent, or Firm* — Spectrum IP Law Group LLC

(57) ABSTRACT

Embodiments disclose an apparatus and methods for biological sample processing enabling isolation and enrichment of microbial or pathogenic constituents from the sample. A vessel for sample containment and extraction is further disclosed for engagement with a transducer capable of efficient sample disruption and lysis. Together these components provide a convenient and inexpensive solution for rapid sample preparation compatible with downstream analysis techniques.

12 Claims, 7 Drawing Sheets

(51) Int. Cl.

| | |
|---|---|
| *G01N 1/40* | (2006.01) |
| *C12N 1/06* | (2006.01) |
| *B01F 31/86* | (2022.01) |
| *C12Q 1/24* | (2006.01) |
| *B01F 101/23* | (2022.01) |

(52) U.S. Cl.
CPC ............ *C12Q 1/24* (2013.01); *G01N 1/4077* (2013.01); *B01F 2101/23* (2022.01); *B01F 2215/0454* (2013.01); *B01L 2200/0631* (2013.01); *B01L 2300/0681* (2013.01); *B01L 2300/0832* (2013.01); *B01L 2400/0439* (2013.01); *G01N 2001/4094* (2013.01)

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,766,067 | A | 8/1988 | Biswas |
| 4,795,699 | A | 1/1989 | Tabor et al. |
| 4,800,159 | A | 1/1989 | Mullis et al. |
| 4,889,818 | A | 12/1989 | Gelfand et al. |
| 4,921,794 | A | 5/1990 | Tabor et al. |
| 4,965,188 | A | 10/1990 | Mullis et al. |
| 4,994,370 | A | 2/1991 | Silver et al. |
| 5,066,584 | A | 11/1991 | Gyllensten et al. |
| 5,091,310 | A | 2/1992 | Innis |
| 5,102,784 | A | 4/1992 | George, Jr. |
| 5,122,464 | A | 6/1992 | Wilson et al. |
| 5,130,238 | A | 7/1992 | Malek et al. |
| 5,142,033 | A | 8/1992 | Innis |
| 5,399,491 | A | 3/1995 | Kacian et al. |
| 5,409,818 | A | 4/1995 | Davey et al. |
| 5,455,166 | A | 10/1995 | Walker |
| 5,648,211 | A | 7/1997 | Fraiser et al. |
| 5,693,233 | A | 12/1997 | Schembri |
| 5,782,878 | A | 7/1998 | Morgan et al. |
| 6,410,278 | B1 | 6/2002 | Notomi et al. |
| 6,509,157 | B1 | 1/2003 | Martinez |
| 6,686,195 | B1 | 2/2004 | Colin et al. |
| 6,743,605 | B1 | 6/2004 | Rabbani et al. |
| 7,056,671 | B2 | 6/2006 | Enoki et al. |
| 8,460,874 | B2 | 6/2013 | Peleg |
| 9,200,317 | B2 | 12/2015 | Tisi et al. |
| 2002/0187547 | A1 | 12/2002 | Taylor et al. |
| 2004/0146933 | A1 | 7/2004 | Quinn et al. |
| 2005/0031499 | A1* | 2/2005 | Meier .................... C12M 45/02 422/128 |
| 2005/0182383 | A1 | 8/2005 | Wallen |
| 2006/0013732 | A1 | 1/2006 | Parthasarathy et al. |
| 2006/0133958 | A1 | 6/2006 | Hsieh et al. |
| 2008/0103297 | A1 | 5/2008 | Parthasarathy et al. |
| 2008/0114304 | A1 | 5/2008 | Nalesso et al. |
| 2010/0056383 | A1 | 3/2010 | Ririe et al. |
| 2010/0086990 | A1 | 4/2010 | Stanley et al. |
| 2010/0147402 | A1 | 6/2010 | Tornqvist |
| 2010/0192706 | A1* | 8/2010 | Fairs .................... B01L 3/502 73/863.23 |
| 2010/0273219 | A1 | 10/2010 | May et al. |
| 2010/0286513 | A1 | 11/2010 | Pollard, Jr. et al. |
| 2010/0288060 | A1 | 11/2010 | Ronsick et al. |
| 2010/0290955 | A1 | 11/2010 | Cho et al. |
| 2011/0009837 | A1 | 1/2011 | Schreiner |
| 2011/0097764 | A1 | 4/2011 | Johnson et al. |
| 2012/0157326 | A1 | 6/2012 | Tisi et al. |
| 2013/0236376 | A1 | 9/2013 | Augstein et al. |
| 2014/0031772 | A1 | 1/2014 | Hardy et al. |
| 2014/0120599 | A1 | 5/2014 | Daub et al. |
| 2014/0272938 | A1 | 9/2014 | Loo et al. |
| 2014/0305196 | A1 | 10/2014 | Ellis et al. |
| 2015/0073348 | A1 | 3/2015 | Bullington et al. |
| 2015/0352545 | A1* | 12/2015 | Taylor .................... B01L 3/508 435/306.1 |
| 2017/0274376 | A1 | 9/2017 | Nobile et al. |
| 2018/0250636 | A1 | 9/2018 | Shindome et al. |
| 2018/0289304 | A1 | 10/2018 | Rogers et al. |
| 2019/0091681 | A1 | 3/2019 | Nobile et al. |
| 2020/0224260 | A1 | 7/2020 | Davidson et al. |

FOREIGN PATENT DOCUMENTS

| | | |
|---|---|---|
| CN | 103789453 B | 3/2016 |
| DE | 102006032637 | 1/2008 |
| EP | 0497272 A1 | 8/1992 |
| WO | 9309250 A1 | 5/1993 |
| WO | 9601327 A1 | 1/1996 |
| WO | 9704126 A1 | 2/1997 |
| WO | 0028082 A1 | 5/2000 |
| WO | 0134790 A1 | 5/2001 |
| WO | 0224902 A1 | 3/2002 |
| WO | 03016569 A1 | 2/2003 |
| WO | 03072805 A2 | 9/2003 |
| WO | 2004027025 A2 | 4/2004 |
| WO | 2004062338 A2 | 7/2004 |
| WO | 2006010948 A1 | 2/2006 |
| WO | 2009004630 A1 | 1/2009 |
| WO | 2010007355 A1 | 1/2010 |
| WO | 2013177429 A2 | 11/2013 |
| WO | 2014153071 A1 | 9/2014 |

OTHER PUBLICATIONS

International Search Report and Written Opinion dated Apr. 29, 2014 for PCT Application No. PCT/US13/075430.
International Search Report and Written Opinion dated Apr. 1, 2016 for PCT Application No. PCT/US15/058612.
Ralf Himmelreich, "Device for the information of biological samples e.g. cells/tissues, comprises sound producing mechanism, which produces sound wave in the sample to be treated, a reception for a container, mixer with a retainer for mix element, and drive" DE102006032637, Jan. 17, 2008 [English translation of Abstract].
Atschul, S. F. et al., J. Molec. Biol. 215:403-410 (1990).
Barany, F. 1991. Proc. Natl. Acad. Sci. USA 88, 189-193.
Barringer, K. Barringer, et al. 1990. Gene 89, 117-122.
Curtis KA, Rudolph DL, Owen SM (2008). "Rapid detection of HIV-1 by reverse-transcription, loop-mediated isothermal amplification (RT-LAMP)". J. Virol. Methods 151 (2): 264-70. doi:10.1016/j.jviromet.2008.04.011. PMID 18524393.
Devereux, J., et al., Nucleic Acids Research 12(1): 387(1984).
EP Examination Report dated May 2, 2018, to TP Patent Application No. 15820668.0.
European Examination Report dated Feb. 28, 2020 to EP Patent Application No. 15821916.2.
Extended European Search Report dated Dec. 4, 2017, to EP Patent Application No. 15821916.2.
First Office Action dated Nov. 5, 2019, to Chinese Patent Application No. 20150059897.8.
Francois P, Tangomo M, Hibbs J, Bonetti EJ, Boehme CC, Notomi T, Perkins MD, Schrenzel J (2011). "Robustness of a loop-mediated isothermal amplification reaction for diagnostic applications". FEMS Immunol. Med. Microbiol. 62 (1):41-8. doi:10.1111/j.1574-695X.2011.00785.x. PMID 21276085.
Gandelman et al., Loop-Mediated Amplification Accelerated by Stem Primers. Int. J. Mol. Sci. 2011; 12(12):9108-9124.
Geojith G, Dhanasekaran S, Chandran SP, Kenneth J (2011). "Efficacy of loop mediated isothermal amplification (LAMP) assay for the laboratory identification of Mycobacterium tuberculosis isolates in a resource limited setting". J. Microbiol. Methods 84 (1): 71-3. doi:10.1016/j.mimet.2010.10.015. PMID 21047534.
Gill, Pooria, et al.; Nucleosides, Nucleotides and Nucleic Acids, 2008. v27(3):224-243.
Guatelli, J. C. Guatelli, et al. 1990. Proc. Natl. Acad. Sci. USA 87, 1874-1878.
Hefner G. J., Yang I. C., Wolter L. C., Stafford M. R., Giffard P. M, BioTechniques, 2001, vol. 30, No. 4, pp. 852-867.
International Search Report and Written Opinion dated Oct. 23, 2015, for PCT/US2015/040792 as filed on Jul. 16, 2015.

(56) References Cited

OTHER PUBLICATIONS

International Search Report and Written Opinion dated Mar. 25, 2020, to PCT Application No. PCT/US19/62189.
Iseki H, Alhassan A, Ohta N, Thekisoe OM, Yokoyama N, Inoue N, Nambota A, Yasuda J, Igarashi I (2007). "Development of a multiplex loop-mediated isothermal amplification (mLAMP) method for the simultaneous detection of bovine Babesia parasites". J. Microbiol. Methods 71 (3): 281-7. doi:10.1016/j.mimet.2007.09.019. PMID 18029039.
Kwoh, D. Y., et at. 1989. Proc. Natl. Acad Sci. USA 86, 1173-1177.
Lizardi, P. M. Lizardi, et al. 1988. BioTechnology 6, 1197-1202.
Lizardi, Paul M. et al., Nature Genetics, 19, 225-232, Jul. 1998.
Macarthur G (2009). Global health diagnostics: research, development and regulation. Academy of Medical Sciences Workshop Report (PDF). Academy of Medical Sciences (Great Britain). ISBN 978-1-903401-20-0.
Mori Y, Kitao M, Tomita N, Notomi T (2004). "Real-time turbidimetry of LAMP reaction for quantifying template DNA". J. Biochem. Biophys. Methods 59 (2): 145-57. doi:10.1016/j.jbbm.2003.12.005. PMID 15163526.
Mori Y, Nagamine K, Tomita N, Notomi T (2001). "Detection of loop-mediated isothermal amplification reaction by turbidity derived from magnesium pyrophosphate formation". Biochem. Biophys. Res. Commun. 289 (1): 150-4. doi:10.1006/bbrc.2001.5921. PMID 11708792.
Nagamine K, Hase T, Notomi T (2002). "Accelerated reaction by loop-mediated isothermal amplification using loop primers". Mol. Cell. Probes 16 (3): 223-9. doi:10.1006/mcpr.2002.0415. PMID 12144774.
Njiru ZK, Mikosza AS, Armstrong T, Enyaru JC, Ndung'u JM, Thompson AR (2008). "Loop-mediated isothermal amplification (LAMP) method for rapid detection of Trypanosoma brucei rhodesiense". PLoS Negi Trap Dis 2 (1): e147. doi:10.1371/journal.pntd.0000147. PMC 2238707. PMID 18253475. open access publication—free to read.
Njiru ZK, Mikosza AS, Matovu E, Enyaru JC, Ouma JO, Kibona SN, Thompson RC, Ndung'u JM (2008). "African trypanosomiasis: sensitive and rapid detection of the sub-genus Trypanozoon by loop-mediated isothermal amplification (LAMP) of parasite DNA". Int. J. Parasitol. 38 (5): 589-99. doi:10.1016/j.ijpara.2007.09.006. PMID 17991469.
Non-Final Office Action dated Oct. 17, 2018, to U.S. Appl. No. 15/326,604.
Non-Final Office action dated Jul. 30, 2019, to U.S. Appl. No. 14/650,529.
Non-Final Office action dated Nov. 1, 2019, to U.S. Appl. No. 16/202,475.
Notomi T, Okayama H, Masubuchi H, Yonekawa T, Watanabe K, Amino N, Hase T (2000). "Loop-mediated isothermal amplification of DNA". Nucleic Acids Res. 28 (12): E63. doi:10.1093/nar/28.12.e63. PMC 102748. PMID 10871386.
Poon LL, Wong BW, Ma EH, Chan KH, Chow LM, Abeyewickreme W, Tangpukdee N, Yuen KY, Guan Y, Looareesuwan S, Peiris JS (2006). "Sensitive and inexpensive molecular test for falciparum malaria: detecting Plasmodium falciparum DNA directly from heat-treated blood by loop-mediated isothermal amplification" Clin. Chem. 52 (2): 303-6. doi:10.1373/clinchem.2005.057901. PMID 16339303.
Puskas et al. "Reduction of Mispriming in Amplification Reactions with Restricted PCR", Genome Research, 1995, vol. 5, pp. 309-311, 1995.
Saiki, R. K. Saiki, et al. 1985. Science 230, 1350-1354.
Sattabongkot J, Tsuboi T, Han ET, Bantuchai S, Buates S (2014). "Loop-mediated isothermal amplification assay for rapid diagnosis of malaria infections in an area of endemicity in Thailand". J. Clin. Microbiol. 52 (5): 1471-7. doi:10.1128/JCM.03313-13. PMID 24574279.
Tanner NA, Zhang Y, Evans TC (2012). "Simultaneous multiple target detection in real-time loop-mediated isothermal amplification". BioTechniques 53 (2): 81-9. doi:10.2144/0000113902. PMID 23030060.
Tomita N, Mori Y, Kanda H, Notomi T (2008). "Loop-mediated isothermal amplification (LAMP) of gene sequences and simple visual detection of products". Nat Protoc 3 (5): 877-82. doi:10.1038/nprot.2008.57. PMID 18451795.
Torres C, Vitalis EA, Baker BR, Gardner SN, Torres MW, Dzenitis JM (2011). "LAVA: an open-source approach to designing LAMP (loop-mediated isothermal amplification) DNA signatures". BMC Bioinformatics 12: 240. doi:10.1186/1471-2105-12-240. PMC 3213686. PMID 21679460. open access publication—free to read.
Walker, G. T. Walker, et al. 1992. Nuc. Acids. Res. 20, 1691-1696.
Walker, G. T. Walker, et at. 1992. Proc. Natl. Acad. Sci. USA 89, 392-396.
Wu, D. Y., et al. 1989. Genomics 4, 560-569.
Office Action Received in Chinese Patent Applcation No. 201580059897.8, dated Nov. 5, 2019, 26 pages, (full translation provided).
Office action dated Sep. 17, 2020, to CN Patent Application No. 201580059897.8.
International Search Report and Written Opinion dated Dec. 8, 2021 for PCT/US2021/045630.
International Search Report and Written Opinion dated Jan. 27, 2022 for PCT/US2021/057146.
Internet webpages, "Tangen Biosciences Closes Oversubscribed $12.2M Series B Preferred Stock Financing," pp. 1-3, Aug. 6, 2020, http://tangenbiosciences.com/2020/08/06/tangen-biosciences-closes-oversubscribed-12-2m-series-b-preferred-stock-financing/.
Soares, R.R.G., et al. "Point-of-care detection of SARS-CoV-2 in nasopharyngeal swab samples using an integrated smartphone-based centrifugal microfluidic platform," medRxiv, Nov. 6, 2020, pp. 1-25.

\* cited by examiner

APPARATUS AND METHOD FOR CELL, SPORE, OR VIRUS CAPTURE AND DISRUPTION

CROSS-REFERENCE TO RELATED APPLICATIONS

This application claims priority to the filing date of PCT Application Serial No. PCT/US15/58612 (filed Nov. 2, 2015), which claims priority to Provisional Patent Application No. 62/074,325, filed on Nov. 3, 2014. Both of applications are incorporated herein in their entirety.

FIELD OF THE DISCLOSURE

The present disclosure is directed generally to inventive apparatus and methods for biological sample processing and analysis. Specifically, the disclosure relates to a method and apparatus for sample disruption and lysis.

BACKGROUND

Rapid and accurate identification of infectious agents in resource limited settings is considered critical for controlling the prevalence and spread of disease. This is especially the case in high burden areas of the globe where economic and technological limitations constrain efficient disease management. Accurate disease diagnosis and pathogen monitoring may involve obtaining and isolating biological materials from a subject or patient sample, for example, in the form of sputum, blood, tissue, urine, or other specimen. Sample extraction techniques may then be employed to isolate or enrich for nucleic acids, proteins or other biological indicators used to detect or identify the presence of a pathogen or infectious agent within the sample.

An important area of disease monitoring relates to respiratory infections, such as pulmonary tuberculosis. Diagnosis, evaluation, and monitoring of subjects may involve collection of sputum samples followed by extraction and isolation of pathogen-originating nucleic acids present in the sample. For such samples it can be challenging to perform sample collection and biomaterial isolation in a manner compatible with downstream processing and analysis techniques. For example, RNA or DNA associated with a suspected pathogen may be desirably enriched to facilitate detection by polymerase chain reaction (PCR), isothermal amplification or other methods. Efficiently breaking down sputum, tissue isolates, and other biological samples can be difficult to perform in a safe and effective manner. Furthermore, low yield isolation protocols may increase the difficulty in detecting the presence of suspected pathogens.

A particular problem exists when attempting to extract and analyze pathogen-identifying nucleic acids from biological samples where the overall amount of the sample or the amount of nucleic acid present in the sample is limited. This problem is further exacerbated in resource limited settings, such as field applications, rural settings, or in underdeveloped communities and countries where lab facilities and sophisticated lab equipment may not be readily available. Providing access to sensitive and accurate biomolecular testing and analysis techniques in these environments continues to be an important challenge to overcome. In this regard, the present disclosure provides significant advances in sample processing and analysis techniques that may improve pathogen monitoring and disease management capabilities in resource-constrained regions of the world.

SUMMARY OF THE DISCLOSURE

Embodiments disclose an apparatus for capturing, disinfecting, and/or isolating microbial or pathogenic components of a biological sample. A sample containment vessel or sample collector is provided to isolate desired components from the sample and may include an integrated filter or separation component. The sample collector may be configured to couple with a mechanical or sonic transducer capable of transmitting energy into the sample sufficient to agitate, disrupt, lyse, and/or homogenize the sample. In various embodiments, the mechanical transducer provides energy sufficient to lyse the sample constituents releasing biomolecules such as nucleic acids and/or proteins that may be subsequently detected by downstream analysis techniques.

An innovative coupling mechanism and configuration between the sample collector and the transducer provides efficient energy transmission into the sample collector. The transducer configuration permits use of mechanical, vibrational, or cavitation-inducing energy generated for example by lower frequency sonic energy as well as higher frequency ultrasonic energy to be applied to the sample providing improved sample processing performance compared to conventional disruption methods. In various embodiments, use of lower frequency sonic energy desirably results in efficient sample homogenization, lysis and release of bimolecular constituents while reducing undesirable degradation of nucleic acids and/or proteins that may be encountered when applying higher frequency ultrasound to a sample. An at least partially or substantially tapered, infundiblular or conical section of the transducer provides efficient energy transduction into the sample collector. The sample collector may be heated and/or cooled while energy is applied to the sample. A lysing fluid may further be utilized to disrupt the sample and release bimolecular constituents of the sample. A filter integrated into the sample collector may additionally be used to capture and/or separate desired biomolecular constituents.

The sample containment vessel or sample collector may comprise various features to facilitate automated or semi-automated sample processing. Additionally, the sample collector and associated instrument components may desirably maintain the sample in an isolated environment avoiding sample contamination and/or user exposure to the sample contents. An integrated filter or separation component may facilitate isolation and concentration of selected sample components, for example, nucleic acids and/or proteins released from cells or dispersed within the sample.

The methods disclosed herein may be applied in connection with downstream analysis techniques including polymerase chain reaction or isothermal amplification methods. A removable reservoir integrated into the sample collector may be used to contain materials such as reaction components and buffers, dilution fluids, sterilization components, preservatives, and/or lysis reagents that can be delivered or mixed with the sample when the sample has been captured or contained within the vessel. An outlet portion of the collector residing on an opposing side of the filter may be used to release the isolated sample constituents from the sample collector while other components of the sample are retained in the sample collector. A valve assembly may be used to provide controllable or selective release of the isolated sample constituents for the outlet portion.

In various embodiments, a portion of the sample collector comprises a sample capture portion that may be configured in a generally or partially cylindrical, tapered, or conical shape. The sample capture portion may further be configured with one or more at least partially tapered, infundiblular or conical sections that couple with or fit into complimentary sections of a transducer configured to transmit energy into the sample containment vessel. In various embodiments, the transducer transmits mechanical, vibrational, or cavitation-inducing energy (for example, in the form of sonic or ultrasonic energy) into the sample fluid or media and is used to disrupt or lyse various components of the sample. The transducer may further heat or cool the sample collector and provide selective release of components that have been captured by a filter. In various embodiments, the sample is disrupted releasing at least a portion of the sample's content or constituents that may pass through the filter.

In various embodiments, the sample collector may contain constituents capable of chemically disinfecting the sample or rendering the sample non-infectious while preserving the integrity of biological constituents such as nucleic acids and/or proteins that may be desirably isolated for subsequent downstream processing and analysis.

In various embodiments, an apparatus is described that permits rapid and semi-automated decontamination, isolation, and extraction of biomolecules, such as nucleic acids and/or proteins from a sample without extensive hands-on processing or lab equipment. The sample preparation apparatus of the present disclosure may further be adapted for use with a portable analytical devices and instruments capable of processing and identifying biomolecules, such as nucleic acids and proteins present in the sample.

In various embodiments, the sample collector and various other components of the system can be fabricated from inexpensive and disposable materials such as molded plastic that are compatible with downstream sample processing methods and economical to produce. Such components may be desirably sealed and delivered in a sterile package for single use thereby avoiding potential contamination of the sample contents or exposure of the user while handling. In various embodiments, the reagents of the sample collector provide for disinfection of the sample constituents and permit sample disposal without substantial contamination risk or remaining remaining infectious or hazardous. The sample collector may be used in simplified workflows and does not require specialized training or procedures for handling and disposal.

In various embodiments, a transducer is configured to couple with the sample collector and facilitates automation of sample processing. The transducer is capable of generates mechanical, vibrational or cavitation-inducing energy (for example, arising from sonic or ultrasonic vibrations) and efficiently disrupts or lyses components of the sample in a safe and isolated manner. The sample collector provides for subsequent delivery of selected sample constituents and reagents in a manner that reduces chances for cross-contamination and transmission of potentially infectious materials.

In various embodiments, an apparatus for sample processing is described. The apparatus comprises: a transducer that generates sonic or ultrasonic energy of a selected frequency, the transducer further comprising an interface having an at least partially tapered conical surface through which the sonic or ultrasonic energy is propagated; and a sample collector having a sidewall at least partially complementary to the interface of the transducer that couples with the interface and receives at least a portion of the sonic or ultrasonic energy generated by the transducer and propagates the sonic or ultrasonic energy into an interior compartment of the sample collector inducing sample cavitation that disrupts or lyses materials disposed within the sample collector.

The apparatus may further be configured with a transducer that comprises a recessed portion in which the interface is disposed, the recessed portion of the transducer dimensioned to receive at least a portion of the sample collector positioning the interface and sidewall in close proximity to thereby propagate the energy generated by the transducer into the interior compartment of the sample collector. Such apparatus may further be configured with the sample collector dimensioned to be removably retained in the recessed portion of the transducer with at least a portion of the sample collector sidewall abuts against the interface to efficiently propagate the energy generated by the transducer.

In still other embodiments, a method for biomolecular extraction from a sample is described where the method comprises: (a) introducing the sample and one or more fluidic reagents into a sample collector through an inlet portion of the sample collector; (b) positioning the sample collector about an at least partially tapered conical interface of a transducer; (c) generating sonic or ultrasonic energy by the transducer that is propagated into the sample collector through the interface wherein the energy induces cavitation in the one or more fluidic reagents and results in at least partial disruption or lysis of the sample releasing nucleic acids or proteins; and (d) collecting at least a portion of the released nucleic acids or proteins through an outlet portion of the sample collector.

The apparatus has the further benefit of concentrating biomaterial of interest. For example, nucleic acids and/or proteins associated with spores, virus, or bacteria present in the sample may be conveniently isolated from the original sample material and concentrated. In some embodiments, portions of the sample may be captured on one or more filters associated with the sample collector 110. Concentration in this manner may desirably increase the efficiency of the downstream assays and analysis improving detection sensitivity or providing lower limits of detection relative to the input sample.

In various embodiments, the automated and semi-automated processing capabilities of the system simplify sample preparation and processing protocols. A practical benefit may be realized in an overall reduction in the number of required user operations, interactions, or potential sample exposures as compared to conventional sample processing systems. This may result in lower user training requirements and fewer user-induced failure points. In still other embodiments, the system advantageously provides effective isolation and decontamination of a sample improving overall user safety while at the same time preserving sample integrity, for example by reducing undesirable sample degradation.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims. It is to be understood that both the foregoing general description and the following detailed description are exemplary and explanatory only and are not restrictive of the scope of disclosed embodiments, as set forth by the claims.

BRIEF DESCRIPTION OF THE DRAWINGS

These and other embodiments of the disclosure will be discussed with reference to the following exemplary and non-limiting illustrations, in which like elements are numbered similarly, and where.

DETAILED DESCRIPTION

Figure 1A:
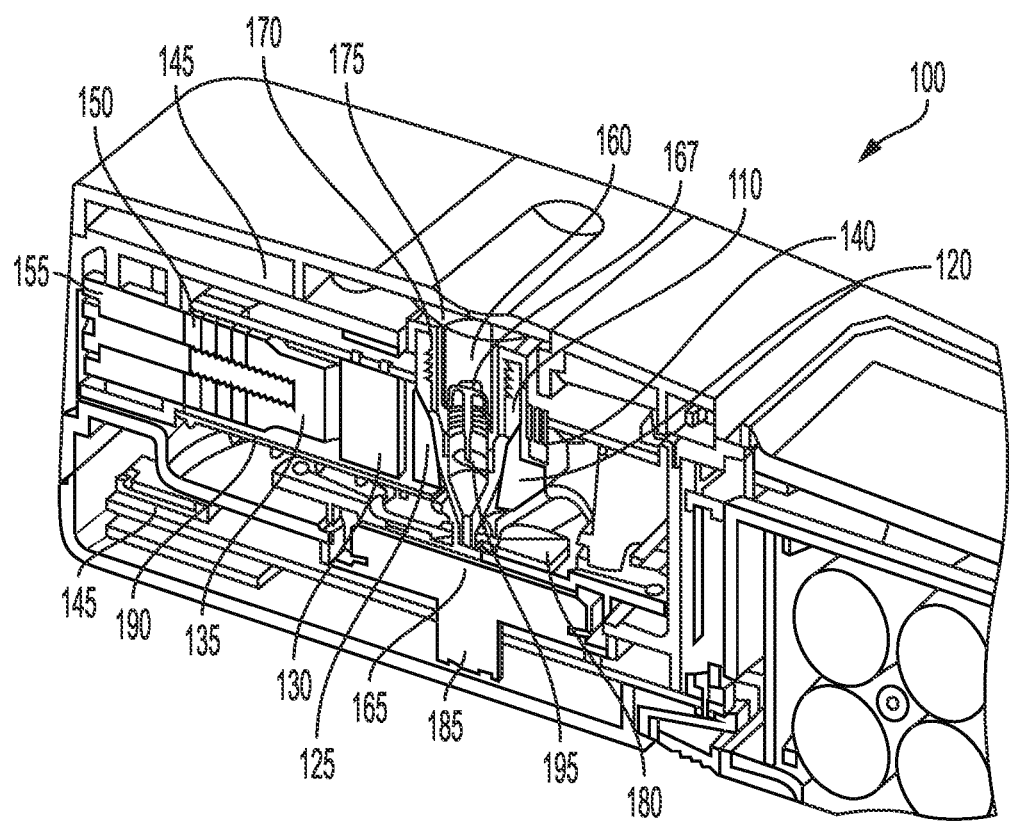
FIG. 1A depicts a cross-sectional view of a sample processing and analysis apparatus according to various embodiments of the present disclosure.

An exemplary cross-sectional view of a sample processing and analysis apparatus 100 is depicted in FIG. 1A. The apparatus 100 may include a sample collector 110 adapted to receive and contain a specimen or sample. In various embodiments, the specimen may comprise a sample or biomaterial such as bodily fluid, urine, blood, stool, sputum, cells, tissue, spores, or other components obtained from a subject or source to be processed and analyzed. Various materials, analytes, or isolates may be desirably recovered from the specimen or sample including by way of example, bacteria or other microorganisms, proteins, nucleic acids, carbohydrates, chemicals, biochemicals, particles, or other components present within the sample or specimen.

As will be described in greater detail hereinbelow, the sample or biomaterial may include infectious, toxic, or otherwise hazardous material that is desirably isolated within sample collector 110 in such a manner so as to minimize or eliminate exposing the user or handler of the sample collector 110 to sample constituents prior to rendering the sample constituents inactive, inert, or in a form that reduces that risk of harm or contamination. As will be described in greater detail hereinbelow, the sample collector 110 design avoids unintended release of sample constituents by leakage from the sample collector 110 including preventing the escape of aerosols or particulates that might otherwise present a contamination risk to the user.

The sample or specimen may further comprise solid, semi-solid, viscous, or liquid materials. In certain embodiments, liquid or fluidic reagents (for example, buffers, water, lysis reagents, or other chemical solutions) may be added to the sample or specimen to aid in propagation of energy to disrupt or lyse the sample. Similarly, solid materials such as beads or particulates may be added to the sample or specimen to aid in disruption or lysis. Materials added to the sample may further include various reagents that facilitate sample dispersion, homogenization, emulsification, or lysis. These materials may further act to render the sample inert, inactive, or sterile. In certain embodiments added materials may chemically or physically react with released sample or specimen components to preserve or prepare the released components for downstream processing.

The apparatus 100 further comprises a cavitation-inducing actuator or transducer 120 configured to receive and orient the sample collector 110 in a desired position within the apparatus 100. The transducer 120 comprises a transducer interface 125 whose geometry and size are generally configured with at least a portion complementary to the sample collector 110. In various embodiments, an exterior surface contour or shape of the sample collector 110 is configured to generally align with and/or be positioned against the transducer interface 125 such that the sample collector 110 is seated or located within a portion of the transducer 120. As will be described in greater detail hereinbelow, the configuration and positioning of the sample collector 110 within the transducer 120 provides a close coupling between the sample collector 110 and the transducer interface 125 thereby permitting efficient energy transfer.

The transducer 120 may further be associated with a heater, chiller or temperature moderating element 130. In various embodiments, a heater is configured to adjustably transmit heat to the sample collector 110 either directly or indirectly. For example, a heating element 130 may comprise a controllable resistive heater embedded within or abutting against an armature 135 of the transducer 120 and capable of transmitting heat energy into the transducer 120. As the transducer armature 135 is heated this energy may further be transmitted through the interface 125 into the sample collector 110. In addition to heating means, the transducer armature 135 may be similarly configured to cool the sample as desired.

The apparatus 100 may further comprise a temperature sensor 140 configured to monitor the temperature of the transducer 120 and/or the sample collector 110. One or more controller boards 145 may receive signals from the temperature sensor 140 and direct operation of the heater/cooler 130 to achieve or maintain a desired temperature within the sample collector 110. In various embodiments, the combined effect of controlled temperature and energy transmission into the sample collector 110 enhances the ability of the apparatus to achieve desired agitation, lysis and/or disruption characteristics for processing of sample constituents contained within the sample collector.

Energy generation by the transducer 120 (for example, sonic or ultrasonic energy) may be provided by one or more coupled piezo devices 150 resulting in controllable vibrations or oscillation of the transducer 120 to provide energy transmission into the sample collector 110. Operation of the piezo devices 150 may further be directed by the controller(s) 145 which may be configured to direct the frequency of operation piezo devices 150 to achieve the desired energy transmission into the sample collector 110. In various embodiments, the transducer 120 may be secured within the apparatus 110 and provided with a tail mass 155 of appropriate weight or configuration to generate a desired or characteristic frequency of oscillation to impart sonic or ultrasonic energy into the sample collector 110.

In various embodiments, the sample collector 110 comprises an inlet portion 160 and an outlet portion 165. The inlet portion 160 may be configured to receive a sample or specimen to be processed within the sample collector 110 and secured with a cap or cover 170 which retains the sample or specimen within the sample collector 110 while preventing the escape of solid, liquid, and/or gaseous materials from the sample collector 110. In various embodiments the cover 170 is secured to the collector 110 in a screw top, snap top, or other securing/locking configuration with sufficient engagement and retention to prevent the escape of material from the sample collector 110 including avoiding formation of aerosols outside of the sample collector 110 that may otherwise contaminate the apparatus 100 or release sample constituents potentially exposing a user to infectious or otherwise dangerous materials found in the sample or specimen.

In various embodiments, positive engagement between the sample collector 110 and the transducer 120 is maintained by a load member 175. The load member 175 may further comprise a spring, button, armature, or other mechanical or electro-mechanical device configured to impart a desired load or force on the cover 170 and sample collector 110 that urges or provides a positive engagement or coupling between the sample collector 110 and the transducer 120 when the sample collector 110 is suitably positioned or aligned with the transducer interface 125.

In various embodiments, the sample collector 110 may be configured with the outlet portion 165 capable of delivering processed sample portions to other components of the apparatus 100 including for example an assay plate 180. The assay plate 180 may further be configured to receive the processed sample and distribute or partition the sample into one or more wells, confinement regions, or chambers associated with the assay plate 180. According to certain embodiments, the assay plate 180 may be engaged by a servo or motor 185 capable of moving or rotating the assay plate and facilitating sample distribution within the assay plate 180.

According to various embodiments, a valve assembly 167 may provide controlled release of processed sample portions to the outlet portion 165 of the sample collector 110. In various embodiments, the valve assembly or actuator 167 may be configured in a normally closed position to retain sample constituents in the sample collector 110 during at least a portion of the duration energy transfer by the transducer 120. The valve assembly 167 may then be opened according to desired processing protocols to release at least a portion on the processed sample or resulting isolates or constituents. In various embodiments, the valve assembly 167 may automatically open based on achieving a desired or selected pressure within the sample collector 110. For example, sample disruption or cavitation may induce a pressure differential in the interior of the sample collector 110 causing the valve assembly 167 to open. Additionally, heat generated in the sample collector interior may cause the valve assembly 167 to open at a selected temperature or temperature range. In another embodiment, gas or vapor generated in the sample collector may cause the valve assembly 167 to open upon achieving a selected pressure or pressure range within the sample collector 110. Gas or vapor generated in the sample collector interior may result from reagents added to the sample collector or mixed with the sample. For example, reagents for generating carbon dioxide, chlorine, chlorine dioxide, nitrogen, or other gases or vapors may be used to actuate the valve assembly 167 and thereby release processed sample constituents in a controlled manner.

In various embodiments, one or more filters 195 may be integrated into the sample collector 110. As will be described in greater detail hereinbelow, these filters 195 may aid in sample separation and/or isolation to retain selected materials within the sample collector 110 while permitting the passage of other materials. For example, sample constituents such as cells, tissue, and lysed residual materials may be desirably retained in the sample collector 110 by the filters 195 while allowing the selective passage of desired sample isolates such as bacteria, viruses, nucleic acids, carbohydrates, and/or proteins. The filters 195 may further have chemical compositions or chemical moieties disposed thereon for selectively retaining various sample materials and may be used to capture and/or separate desired constituents as will be appreciated by those of skill in the art.

The apparatus 100 may further include one or more assay plate heating/cooling elements 190 to maintain the assay plate 180 at desired temperature ranges. Configurable heating and/or cooling in this manner may aid in performing sample reactions using various reagents and protocols. For example, processed sample received from the sample collector 110 may comprise concentrated and/or purified nucleic acids to be subjected to polymerase chain reaction or probe-based nucleic acid detection techniques within the assay plate 180 for detection and/or identification of selected sample constituents.

An exemplary sample processing system that may be adapted for use with the sample collector 110 and sonic transducer 120 for automated or semi-automated sample processing is described in commonly assigned PCT Application Serial PCT/US2013/075430 (Publication #WO2014093973) entitled "METHOD FOR CENTRIFUGE MOUNTABLE MANIFOLD FOR PROCESSING FLUIDIC ASSAYS" to John *Nobile*, the contents of which are hereby incorporated by reference in its entirety. It will be appreciated by those of skill in the art that the methods and apparatus of the present disclosure may be adapted to other platforms and configurations for sample processing and as such other embodiments and adaptations are considered within the scope of the present teachings.

Figure 1B:
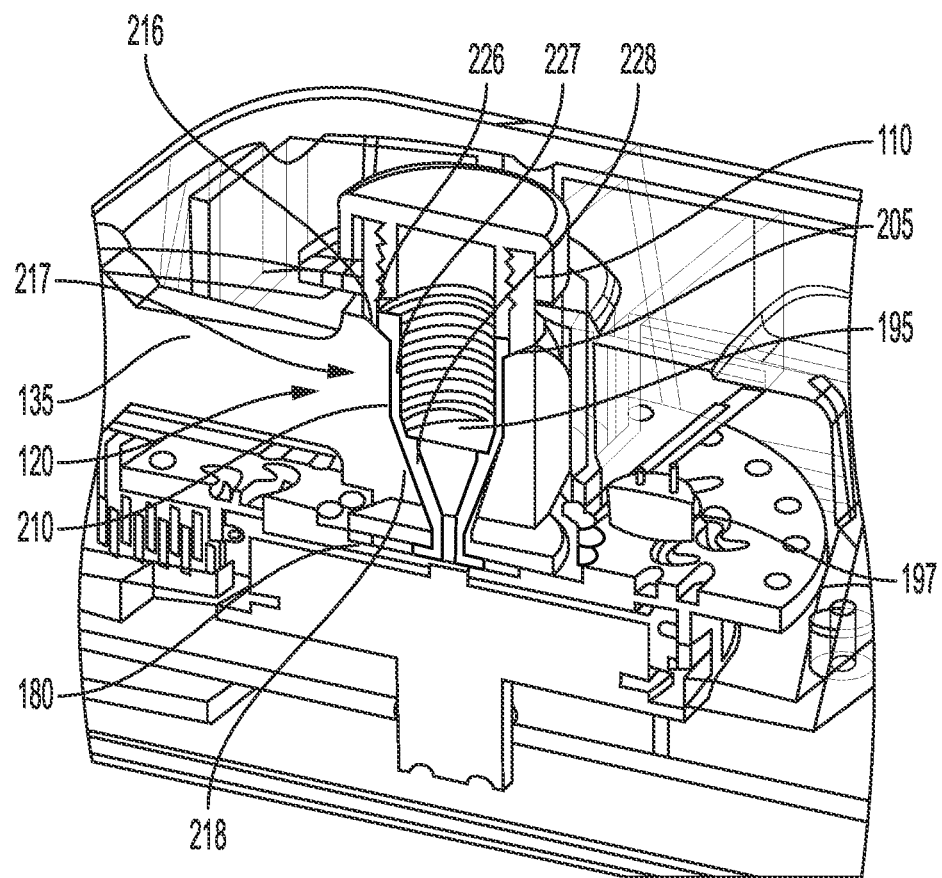
FIG. 1B depicts another cross-sectional view of a sample processing and analysis apparatus illustrating engagement between a sample collector and a transducer according to various embodiments of the present disclosure.

FIG. 1B depicts another cross-sectional view of the apparatus 100 depicting an exemplary configuration and engagement between the sample collector 110 and the transducer 120. Unlike conventional transducer designs that may include a relatively small horn or projection with a generally flat surface for energy transmission into a sample, the transducer 120 of the present teachings employs an innovative structure including an at least partially or substantially tapered, infundiblular or conical recess/cavity 205 associated with the armature 135 that is capable of receiving or coupling with the sample collector 110. In various embodiments, the recess or cavity 205 of the transducer 120 is dimensioned and/or shaped in a manner that permits the sample collector 110 to be positioned within or in proximity to the recess 135 whereby a sidewall or portion 210 of the sample collector 110 engages with the transducer 120 at the interface 125. In various embodiments, a close coupling between the transducer 120 and sample collector 110 is achieved by forming the recess 135 of the transducer 120 to house or contain a portion of the sample collector 110 such that the sample collector 110 is at least partially inserted into or resides within the recess 135. In various embodiments, the transducer interface 135 may comprise a plurality of surface contours, curvatures, or angles (exemplified by elements 216, 217, 218) that align with or are complimentary to sidewall surfaces, curvatures, or angles of the sample collector 110 (exemplified by elements 226, 227, 228). In various embodiments, configuration of the transducer 120 with an at least partially or substantially tapered, infundiblular or conical recess 205 desirably improves energy transmission between the transducer 120 and the sample collector 110.

One particular advantage provided by the at least partially or substantially tapered, infundiblular or conical transducer design of the present teachings is that lower frequency energy or vibrations may be efficiently transmitted into the sample collector 110. Conventional ultrasonic horns are typically configured with a relatively small area for engagement between the horn and the surface into which energy is transmitted. Such configurations may be necessary in part to insure sufficient propagation of the ultrasonic energy and consequently provide limited or highly focused energy transmission into the sample. Such modes of energy transmission may impose significant limitations on how much of a sample may receive the energy. In applications where a sample is to be mixed, disrupted, or lysed, the relatively small or limited contact surface between the ultrasonic horn and the sample collector results in potentially reducing the overall volume or amount of sample that can be processed and may further result in incomplete or ineffective sample mixing, disruption or lysis.

In accordance with the present disclosure, an innovative transducer design overcomes the limitations of conventional transducer designs increasing the overall surface engagement or contact between the transducer 120 and the sample collector 110. In various embodiments, the close coupling of the transducer 120 with the sample collector 110 along or about one or more surfaces, such as provided by complimentary and at least partially or substantially tapered, infundiblular or conical designs, desirably increases the overall amount of contact between the two components and provides for improved energy transmission into the sample collector 110. Consequently, operations including for example, sample mixing, disruption, or lysis can be performed more efficiently, with less power, and/or more uniformly.

In various embodiments, due at least in part to the improved or efficient energy transfer between the transducer 120 and the sample collector 110, sample processing operations such as cellular lysis or disruption to break down or disperse the sample constituents can be achieved without the use of beads or other particulates added to the sample for purposes of enhancing the efficiency of these processes. Avoidance of beads and other particulates also desirably reduces costs, simplifies processing protocols and avoids potential clogging of filters or membranes that may be used in sample processing.

Despite not requiring particulates for sample processing, the transducer 120 and sample collector 110 designs of the present disclosure may accommodate use of particulates dispersed within the sample to aid in lysis. In particular, abrasive particles or beads of various dimensions and compositions may be used according desired processing protocols. Such particulates may comprise polymeric materials such as polystyrene, polypropylene, acrylic-based materials, etc. Additionally, the particulates may be silica-based, silicone-based, metal, glass, or other materials depending on the reactivity of the sample and the desired application. The size or diameter of the particulates may further vary depending upon the application and may, for example, be in the size range of approximately 0.1-1 microns in diameter, 1-10 microns in diameter, 10-100 microns in diameter, 100-1000 microns in diameter, or greater than 1000 microns in diameter. Similarly, the total amount of particulates loaded with the sample may vary depending on the amount or type of sample. In various embodiments, particulates may comprise approximately 1-10% of the sample volume, 10%-25% of the sample volume, 25-50% of the sample volume, or more than 50% of the sample volume.

In various embodiments, the transducer 120 may be configured with more than one recess or sample collector coupling area 135. For example, the transducer 120 may be configured to receive two, three, four, or more sample containers 110 into which energy is simultaneously applied. Additionally, the transducer 120 may be configured to couple with other configurations of sample containers capable of discretely retaining multiple samples such as multiwell plates, microarrays having multiple sample containment regions, or other vessels or consumables for which suitable designs for the transducer 120 may be readily configured. The shape and size of the sample collector 110 and the corresponding complementary surfaces of the transducer 120 may be adapted to suit many different applications. For example, the sample container 110 may be configured with one or more generally cylindrical, conical, cuboid, pyramidal, or prismatic surfaces. These surfaces may further include an at least partially tapered or narrowed region or section.

In various embodiments, the configuration and dimensions of surfaces facilitate positioning of the sample collector 110 within the recess or coupling area 135 of the transducer 120. For example, an at least partially tapered or conical sample collector 110 may be approximately or roughly positioned above the transducer 120 and deposited within the recess in such a manner that the sample collector 110 and transducer 120 readily align or orient with respect to one another to provide improved contact or engagement between complimentary elements (depicted for example by the engagement between elements 216, 217, 218 and 226, 227, 228 in FIG. 1B) without having to precisely align the surfaces manually. The guided or self-aligning design of the sample collector 110 with respect to the transducer 120 is particularly advantageous for use in portable and field instruments where environmental conditions or anticipated usage requirements may not be conducive to precise alignment by a user.

Figure 2B:
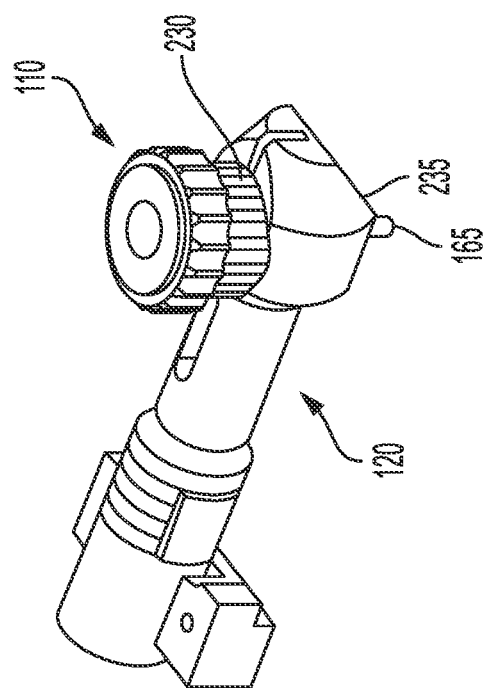
FIG. 2B depicts another perspective view of the exemplary sample collector and transducer design in an engaged or closed position according to various embodiments of the present disclosure.
Figure 2A:
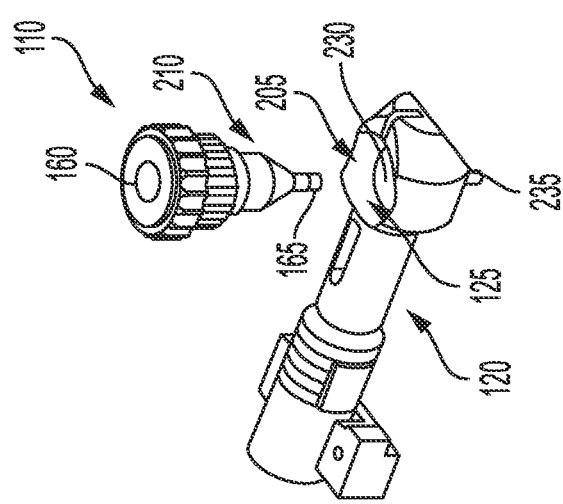
FIG. 2A depicts a perspective view for an exemplary sample collector and transducer design in an open configuration according to various embodiments of the present disclosure.

FIGS. 2A-B depict perspective views for exemplary sample collector 110 and transducer 120 designs according to the present teachings. As shown in FIG. 2A, the transducer recess 205 is formed by the interface 125 with surface contours (corresponding to elements 216, 217, 218 in FIG. 1B) that are complementary to or proportioned in a manner similar to at least a portion of the sidewalls 210 of the sample collector 110 (corresponding to elements 226, 227, 228 in FIG. 1B). As discussed above, the sample collector 110 may comprise a generally conical taper to facilitate insertion or locating about the transducer recess 205.

The transducer recess 205 may further comprise openings 230, 235 permitting convenient insertion or placement of the sample collector 110 within or about the recess 205. In various embodiments, at least a portion of the sample collector 110 may extend outside of the transducer openings 230, 235 in such a manner so that the transducer surfaces do not directly contact the sample collector openings 160, 165. Such a configuration desirably isolates or reduces potential exposure of the transducer surfaces to sample constituents that may be contained in the sample collector 110.

Additionally, the transducer 120 may be configured to transmit energy into the sample collector 110 at substantially the same time as sample constituents or reagents are deposited into or withdrawn from the sample collector 110. In an exemplary embodiment, sample constituents may be eluted from the sample collector 110 and deposited into a multiwall plate, microarray, or other sample receiving component while the transducer 120 is in operation. Operation of the transducer 120 and concomitant energy transmission into the sample collector 110 may further induce, enhance, or encourage sample constituents to exit the sample collector 110. In various embodiments, active energy transferred into the sample collector 110 by the transducer 120 during elution or removal of sample constituents may be desirable in instances where at least a portion of the sample constituents comprise viscous, particulate, or tacky materials.

FIG. 2B depicts an exemplary positioning of the sample collector 110 within the recess 205 of the transducer 120 where at least a portion of the sidewalls 210 of the sample collector 110 reside in close proximity or are in contact with the transducer interface 125. As previously described, portions of the sample collector 110 may extend beyond or outside of the openings 230, 235 of the transducer 120 as shown in the Figure where the outlet portion 165 of the sample collector 110 extends from the recess 205. Configured in this manner the sample collector 135 may be coupled directly or indirectly with other apparatus components including by way of example downstream sample processing consumables such as an array, microwell, sample receiving module, or other devices (not shown in the Figure) as will be understood by those of skill in the art. In various embodiments, engagement of the sample collector 110 with the transducer 120 may include a latch, spring, or screw member that secures or positions these components in a desired orientation or with a desired positive pressure or coupling force to insure efficient energy distribution into the sample collector 110. The securing or positioning component may be integrated into the sample collector 110 and/or the transducer 120 or alternatively be provided by an exterior member such as the previously described spring or latch 175 shown in FIG. 1A. Providing a securing component in this manner may be advantageous where the apparatus is a portable or field operative device that is subject to jarring, external vibrations or other conditions that may disengage or dislocate the sample collector 110 from the transducer 120 in undesired manners and/or before sample processing is complete.

Figure 3:
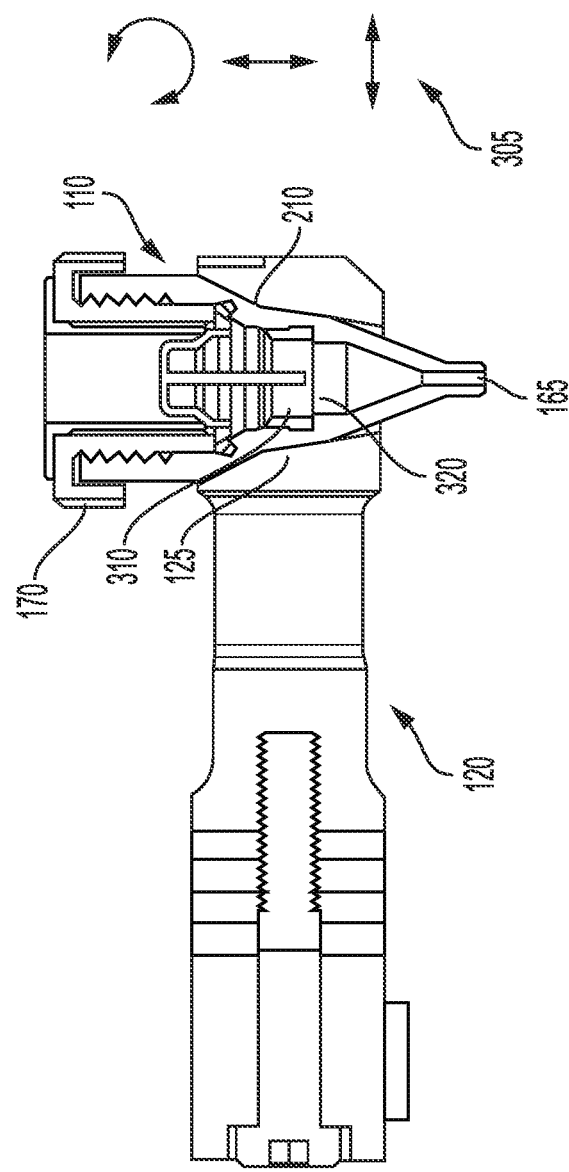
FIG. 3 depicts a cross-sectional view of an exemplary transducer coupled or engaged with a sample collector according to various embodiments of the present disclosure.

FIG. 3 depicts another cross-sectional view of the transducer 120 with the sample collector 110 in a coupled or engaged position. As illustrated, one or more transducer interface surfaces, for example shaped or configured as one or more at least partially tapered, infundiblular or conical sections, are in close proximity or engaged with the sidewalls 210 of the sample collector 110 providing efficient energy transfer into the sample collector interior and sample constituents and/or reagents contained therein. Various modes of vibration or energy transfer may be induced within the transducer 120 as illustrated by the motion or force vectors 305. In addition to generally linear motion or vibration, circular or other patterns or combined patterns of motion may be imparted to the sample collector 110 by the transducer 120.

Ultrasonic energy waves have a frequency above 20 kHz. Ultrasonic disruptors employing a probe or horn-based probe for energy transmission may operate in a frequency from 50 kHz to 500 kHz, and frequencies may extend into the range from about 0.5 MHz to about 5 MHz. In various embodiments, the transducer designs and methods of the present disclosure are configured to operate both at sub-ultrasonic frequencies and also ultrasonic frequencies. In various embodiments, sonic frequencies may be sub-20 kHz, sub-15 kHz, sub-10 kHz, sub-5 kHz, or less. According to the present disclosure, the various transducer configurations described herein desirably provide efficient sonic energy transmission and propagation properties. Conventional probe or horn-based designs do not propagate lower frequency sonic energy efficiently and as a result sonic energy has not been widely used conventionally. This may be due in part to the lower efficiency disruption and lysis properties of sonic energy when applied by conventional transducer designs. The transducer designs of the present disclosure overcome the limitations of conventional transducer designs and provide for efficient sonic and ultrasonic energy transmission and propagation properties.

Another significant advantage realized using relatively low frequency sonic energy is that the size of cavitation bubbles formed in a liquid medium may be increased relative to ultrasonic frequencies. Cavitation bubbles arise where vibrational or mechanical energy propagates through a liquid or fluidic medium. Cavitation bubbles are formed and grow when a liquid is put in significant state of tension. Acoustic pressure waves transmitted by energy transmission from a transducer result in the liquid undergoing a compression and rarefaction cycle. During rarefaction, pressure in the liquid becomes negative and when the negative pressure falls below the vapor pressure of the fluid medium, the energy wave may cause voids or cavitation bubbles to form in the medium. The size of the bubbles formed affects the efficiency of sample disruption or sample lysis.

In various embodiments, it is desirable to generate relatively large cavitation bubbles to enhance agitation, disruption, and/or lysis properties of energy transmitted by the transducer. According to the present disclosure, sonic energy may be efficiently transmitted into an at least partially liquid, viscous, or fluidic sample to create larger cavitation bubbles than conventional ultrasonic disruptors. It will be understood, that while the transducer designs of the present disclosure are particularly suitable for sonic energy generation and transmission into a sample, these designs may be adapted for use with higher frequency acoustic and mechanical energy ranges such as ultrasonic or megasonic applications without departing from the scope of the present teachings.

In various embodiments, suitable frequency parameters for the transducer may be in the range of approximately 20 kHz or less. In some embodiments, the transducer may be operated in the range of approximately 17.5 kHz. In still other embodiments, the transducer may be operated in the range of 15 kHz or less. For the operating frequencies described above, the transducer may be operated at approximately 400 volts or less, 200 volts or less, or 100 volts or less. Efficient sample disruption may further be provided by operation of the transducer over brief time intervals. For example, energy may be applied to a sample in multiple short intervals for example, between 1-10 intervals of approximately 60 seconds or less. In other embodiments, between approximately 4-8 intervals of transducer operation for 20-40 seconds may be used. In some embodiments, relatively short pauses between application of energy to the sample may take place. For example, pauses between approximately 1-5 minutes or less between energy application intervals may be applied preventing sample over-heating. In some embodiments, pauses of approximately 1 minute or less with energy application intervals of approximately 1 minute or less in a frequency range of approximately 20 kHz or less may result in sufficient lysis of a sample. For example, 4-6 intervals of transducer operation for 30 seconds to 1 minute at approximately 15-20 kHz cycles with 30 sec-1 minute pause cycles may result in lysis efficiency of over 90% for bacterial samples such as *Mycobacterium smegmatis* and Tuberculosis *mycobacterium*.

In various embodiments, a sample to be processed may be inserted into an upper portion or sample retention region 310 of the collector 110. The sample along with various reagents, disinfectants, buffers, and other constituents may then be subjected to a desired disruption or lysis protocol. Operation of the transducer 120 may occur at various desired frequencies, temperatures, and/or time intervals such that the sample is mixed with other constituents over a first interval and lysis or sample disruption takes place over a second interval. As previously described, sample disruption or lysis may release biomolecules or other constituents into a fluidic volume of the sample retention regions 310. As will be appreciated by those of skill in the art, numerous protocols and/or methods may be adapted for use with the collector 110 including multistep protocols such as those which involve a sample lysis step followed by a capture and/or elution step to isolate compounds, chemicals, or sample constituents of interest.

A filter, size exclusion membrane, selective chemical/molecular capture surface, or other separation component 320 may be integrated into the sample collector 110. In various embodiments, the separation component 320 may be positioned generally below the sample retention region 310 and provide the ability to separate, capture, or selectively elute desired chemicals, biomolecules, or other constituents from the sample. Certain sample constituents may further be retained in the collector 110 and others passed through the collector outlet 165 thereby isolating, purifying and/or concentrating desired materials from the sample. As previously discussed, and in various embodiments, nucleic acid and/or protein constituents may be isolated from a biological specimen and eluted from the collector 110 into a separate array, microwell, or other sample collection device for further processing and analysis.

The transducer configurations of the present teachings desirably provide improved energy transmission properties compared to conventional ultrasonic disruptors. In certain configurations, the structure and shape of the transducer interface 125 provide enhanced energy transmission properties for both lower frequency sonic energy vibration or mechanical oscillation and ultrasonic energy. An innovative aspect of the transducer design permits relatively low frequency sonic energy (e.g. sub-ultrasonic range) to be transmitted into the collector 110 in an efficient manner facilitating sample disruption and lysis.

Figure 4A:
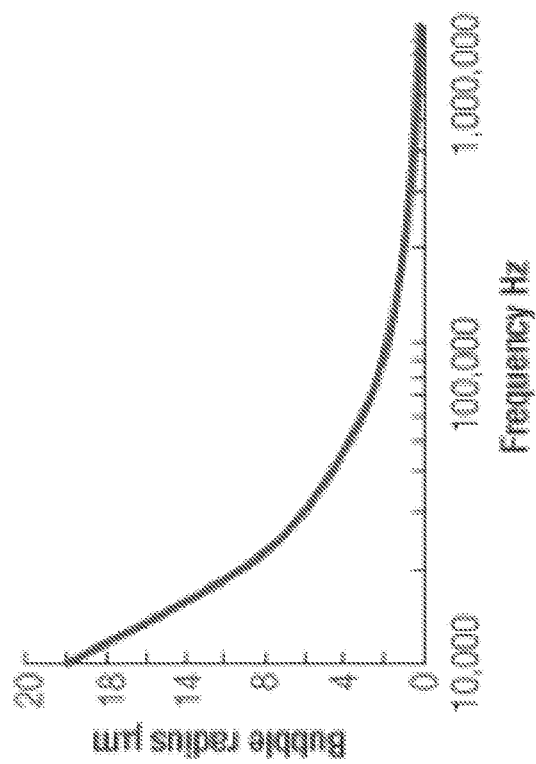
FIGS. 4A & 4B are representative graphs of average bubble size formed in a liquid over a range of transducer frequencies according to various embodiments of the present disclosure.
Figure 4B:
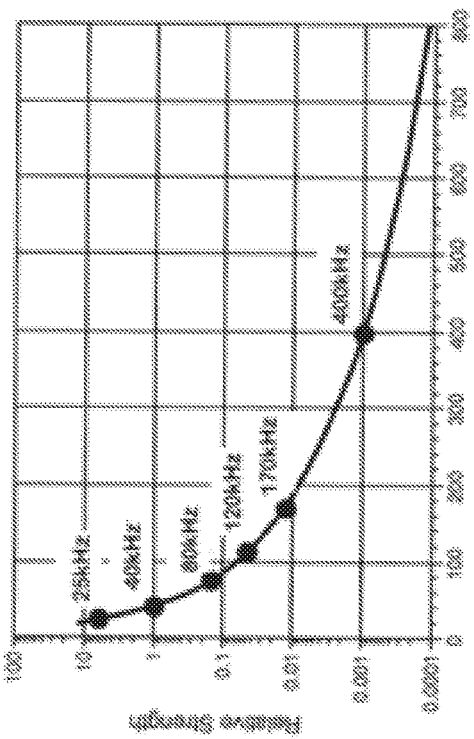
Figure 4C:
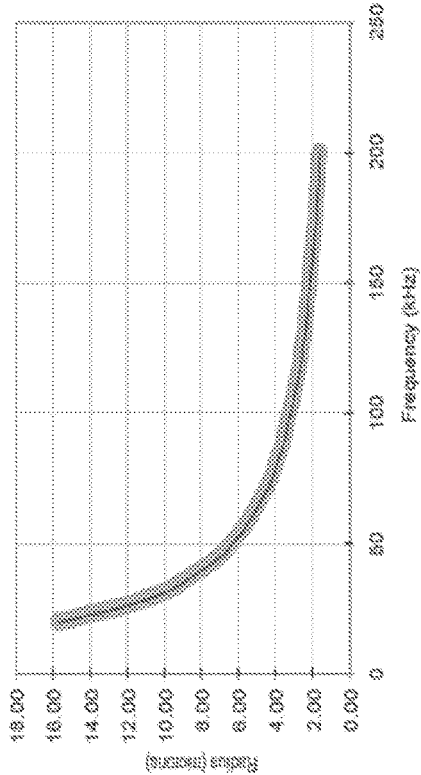
FIG. 4C is a representative graph of relative strength or efficiency of energy transfer into a fluidic volume versus transducer oscillation frequency according to various embodiments of the present disclosure.

FIGS. 4A-C illustrate exemplary characteristics of sonic energy transfer that provide for improved sample processing according to the present teachings. Vibrational or mechanical transmission into a liquid sample may result in the formation of bubbles within the liquid. The size of the bubbles may further affect the mixing, shearing, or lysis properties within the sample when subjected to a selected range of energy transmissions. In various applications, it is desirable to generate relatively large bubbles to improve the energy transmission properties into the sample and/or to generate a desired mechanical effect (e.g. disruption, lysis, or sheering) on the sample constituents. For example, when disrupting or lysing thick or viscous samples such as sputum, blood, or tissue it may be desirable to maintain a bubble population with a size larger than typically provided by ultrasonic energy transmission.

According to the present teachings, larger bubbles and/or more efficient mixing and/or lysis of a sample can be achieved using lower frequency sonic energy transmission as compared to ultrasonic energy transmission. Sonic energy transmission may also be less disruptive or damaging to various sample constituents such as nucleic acids and/or proteins reducing the overall fragmentation of these molecules and preserving their integrity during sample processing.

FIGS. 4A & 4B are representative graphs of average bubble size formed in a liquid over a range of transducer frequencies. At higher frequencies (approximately in the range of 100 kHz or more) bubble size is markedly reduced compared to bubbles formed at lower frequencies (approximately in the range of less than 100 kHz). In particular, bubbles formed in the range of 20 kHz or less may be several times the size or volume of bubbles formed at higher frequency ranges. Larger bubbles may improve the sample processing characteristics and energy transmission properties of the transducer obviating the need to include beads or other particulates in the sample or carrier fluid which are conventionally used to enhance mixing and/or lysis.

FIG. 4C is a representative graph of relative strength or efficiency of energy transfer into a fluidic volume versus transducer oscillation frequency. At higher frequencies (e.g. in the ultrasonic range) overall energy transmission is relatively low as compared to lower frequencies (e.g. in the sonic range). Notably, at frequencies lower than 20 kHz, overall energy strength can be several orders of magnitude greater than at frequencies higher than 100 kHz. An innovative aspect of the present teachings is the recognition that lower frequency energy transmissions when suitably applied to the sample may therefore give rise to improved sample disruption and lysis properties. Thus, by configuring the transducer 120 to accommodate efficient low frequency energy transmission into the sample collector 110, enhanced sample disruption and lysis may be achievable relative to conventional ultrasonic energy applications.

Figure 5B:
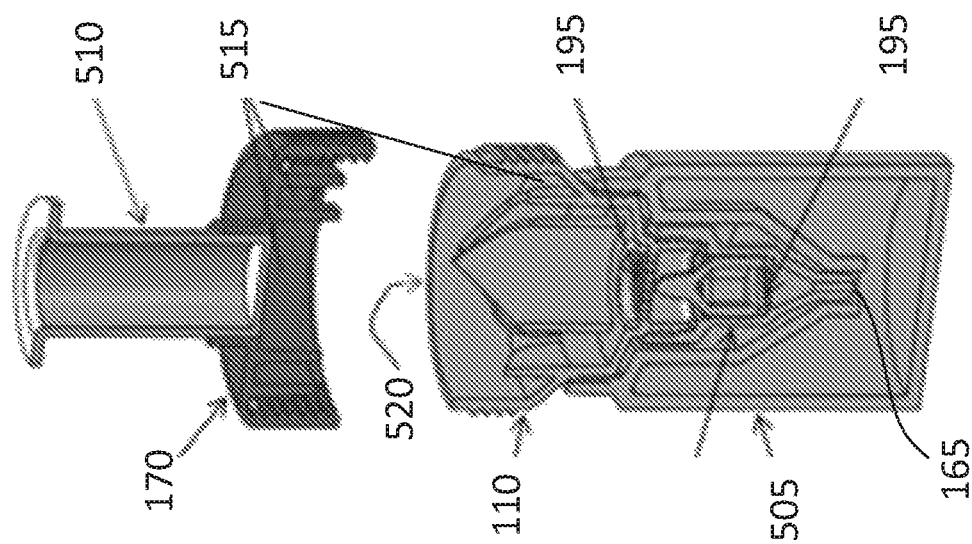
FIGS. 5A-C illustrate exemplary embodiments of a sample collector that may be adapted for use with a sonic transducer according to various embodiments of the present disclosure.
Figure 5A:
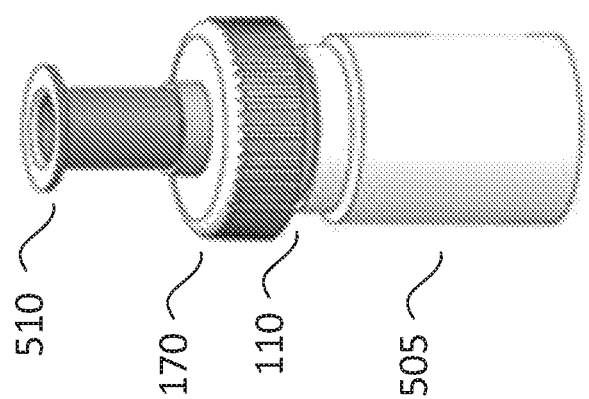
Figure 5C:
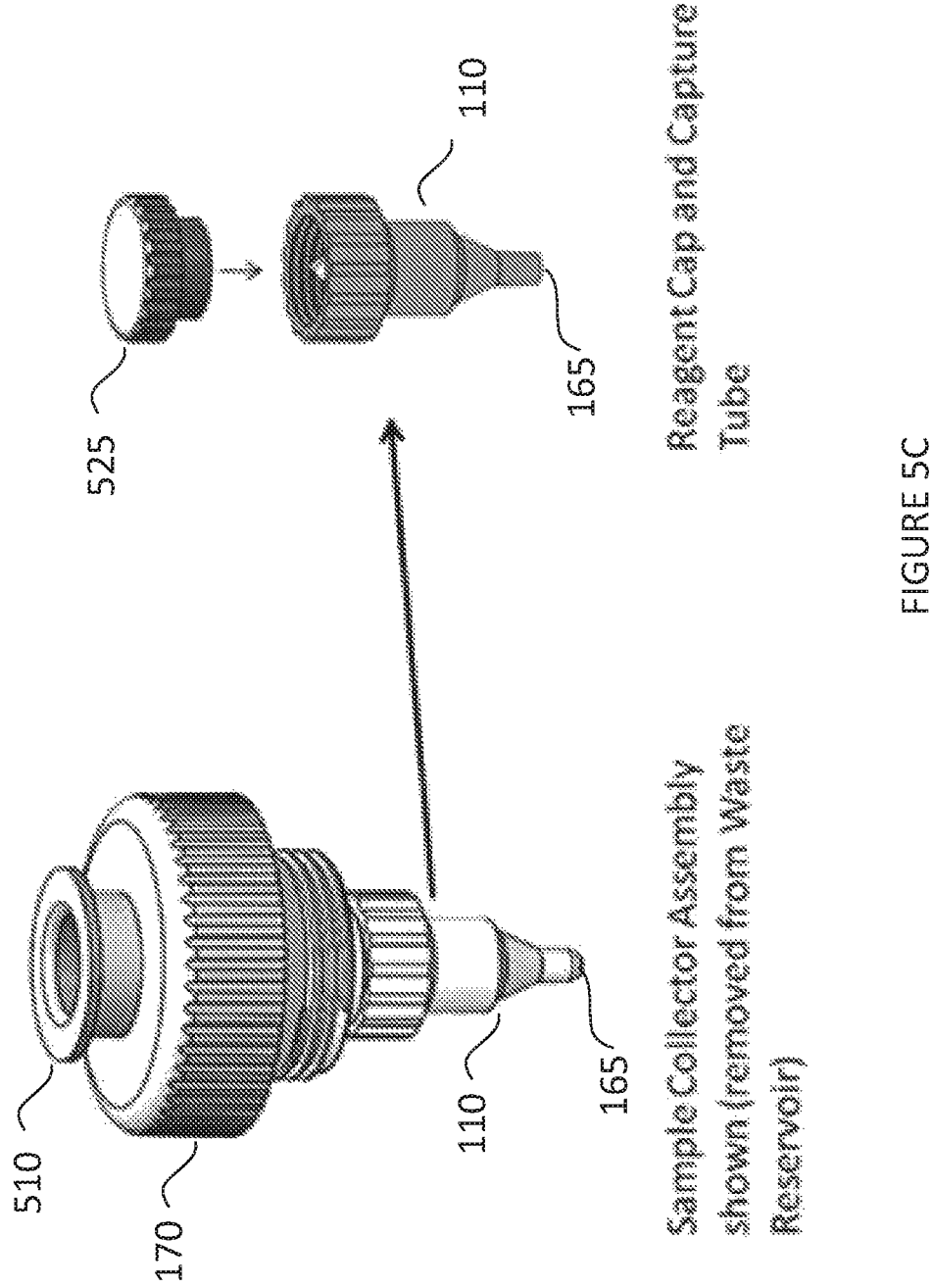

FIGS. 5A-C illustrate exemplary embodiments of a sample collector 110 that may be adapted for use with the transducer designs of the present disclosure. A cap or cover 170 and a waste or liquid reservoir 505 may couple or engage with the sample collector 110. In various embodiments, these components form an integrated device that may be used to collect, house, and/or store a sample to be later processed using the transducer 120. FIG. 5A depicts the sample collector 110 in a closed or sealed arrangement with the cover 170 and liquid reservoir 505. In this configuration, sample material may be desirably contained within a sample retention volume of the sample collector 110 and isolated preventing contamination or leakage of the sample constituents.

As shown in the open sample collector arrangement in FIG. 5B, the cover 170 may further comprise a plunger or button 510 used to mix or position sample constituents and/or reagents within the internal collector volume. In certain embodiments, the cap or cover 170 or a portion of the collector 110 may be adapted to house one or more reagents that are desirably mixed with the sample constituents. For example, the cover 170 may contain, store, or sequester one or more different reagents that are contained in one or more compartments 515. Alternatively, these compartments 515 may be integrated into the collector 110. The reagents may further be isolated, preserved, and/or separately contained using an adhesive or heat sealed film or foil or by other means as will be appreciated by those of skill in the art.

In various embodiments, the plunger 510 and/or other components of the sample collector 110 may include a piercing or opening member 520 capable of releasing the reagents when the sample is added to the collector 110. The waste or liquid reservoir 505 may further provide sufficient support to act as a stand or holder when fitted to the sample collector 110 and in various embodiments encloses the collector opening 165, filters 195, and other components of the sample collector 110. The reservoir 505 may also be snapped or screwed onto the sample collector 110, for example with with a non-airtight fit to the bottom opening 165 of the sample collector allowing venting.

One or more of the filters 195 may be positioned in assemblies about the collector 110 and along with the cover 170 and/or liquid reservoir form a substantially air or liquid impermeable seal or closure preventing undesired leakage from the collector 110. In various embodiments, selected components or parts such as the cover 170 or reservoir 505 may engage with the collector 110 using mated threads and may be sealed for example by precision mating surfaces or elastomeric seals. In various embodiments, the filters 195 may be designed to catch or retain biomaterials such as spores or bacteria of a certain minimum size, for example, above 0.2 um, but let liquid, particulates, and other reagents pass through when sufficient hydrostatic pressure is applied. Such hydrostatic pressure may be generated by the plunger 510 or by various other means including cavitation or heating of the sample by the transducer 120.

In various embodiments, the sample collection device 110, including the one or more filter assemblies 195, may be designed to directly accept the sputum or other biological sample from a subject. As shown in FIG. 5C, in various embodiments, after the sample is captured in the sample collector 110, a first reagent supply cap 525 may be coupled to the sample collector 110. Such an approach desirably allows reagents to be added to the sample or specimen in a safe and non-disruptive manner reducing the likelihood of user or device contamination and further avoids aerosol formation. As the reagent cap 525 is secured or positioned on or within the collector 110 one or more reagent reservoirs within the cap 525 may be punctured or opened by piercing features 520 in the sample collector 110 as previously described.

In various embodiments, the reagents may be designed to mix or react with the sample for purposes of preservation or performing chemical reactions. For example, a sputum sample may be mixed with reagents selected to dilute and/or liquefy the sputum, neutralize or lyse microbes present in the sample, and/or render the sample non-infectious. Another function of the one or more reagents may, in various embodiments, engage in a chemical reaction that will evolve a gas to generate an increased pressure within the sample collector 110. The increased pressure may be sufficient to push or drive portions or substantially all of the sample through the one or more filters 195 into the liquid reservoir or tank 505. In various embodiments, passage of the sample through the one or more filters 195 may trap or isolate some or substantially all of the desired microbes or other materials on the filters 195. An alternative method of passing the liquefied sample through the filters 195 is for the reagent delivery cap 525 to contain a plunger 510 that would be actuated by the user at such time when the reaction is complete.

While the principles of the disclosure have been illustrated in relation to the exemplary embodiments shown herein, the principles of the disclosure are not limited thereto and include any modification, variation or permutation thereof.

What is claimed is:

1. An apparatus for sample processing comprising:
   a transducer that generates sonic or ultrasonic energy of a selected frequency, the transducer further comprising an interface that includes a tapered surface forming a conical cavity; and
   a sample collector with a conical portion configured to be received by the cavity and having a sidewall at least partially complementary to the tapered surface, the interface coupling the transducer to the sample collector such that at least a portion of the sonic or ultrasonic energy generated by the transducer can be propagated into an interior compartment of the sample collector through the tapered surface.

2. The apparatus of claim 1, wherein the sample collector is dimensioned to be removably retained in the cavity with at least a portion of the sample collector sidewall abutting against the interface to propagate the energy generated by the transducer.

3. The apparatus of claim 1, wherein the sample collector comprises an inlet portion and an outlet portion, the inlet portion dimensioned to receive a sample, the outlet portion dimensioned to dispense at least a portion of the sample.

4. The apparatus of claim 3, wherein the sample collector further comprises one or more filters to provide selective passage of the sample therethrough.

5. The apparatus of claim 1, further comprising a sample having biomaterial disposed in the sample collector, wherein the sonic or ultrasonic energy transmitted by the transducer is capable of at least partially lysing the biomaterial to release a quantity of disrupted or lysed material.

6. The apparatus of claim 5, wherein the biomaterial comprises cells, spores, or viruses from which nucleic acids or proteins are released by disruption or lysis of the sample.

7. The apparatus of claim 5, wherein the disrupted or lysed material further comprises nucleic acids or proteins.

8. The apparatus of claim 1, wherein the selected frequency of the sonic or ultrasonic energy generated by the transducer is less than 50 kHz.

9. The apparatus of claim 8, wherein the selected frequency of the sonic or ultrasonic energy generated by the transducer is less than 20 kHz.

10. The apparatus of claim 1, wherein the transducer generates heat and cavitation-inducing energy to propagate into the sample collector.

11. The apparatus of claim 1, further comprising a quantity of sample disposed in the sample collector.

12. The apparatus of claim 11, wherein the sonic or ultrasonic energy is configured to induce cavitation in the quantity of sample disposed in the sample collector.

* * * * *